(12) United States Patent
Avory et al.

(10) Patent No.: US 8,865,125 B2
(45) Date of Patent: Oct. 21, 2014

(54) RADIOIODINATION METHOD

(75) Inventors: Michelle Avory, Amersham (GB); William John Trigg, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 112 days.

(21) Appl. No.: 13/388,464

(22) PCT Filed: Aug. 20, 2010

(86) PCT No.: PCT/EP2010/062149
§ 371 (c)(1),
(2), (4) Date: Feb. 2, 2012

(87) PCT Pub. No.: WO2011/020907
PCT Pub. Date: Feb. 24, 2011

(65) Prior Publication Data
US 2012/0134923 A1 May 31, 2012

Related U.S. Application Data

(60) Provisional application No. 61/235,393, filed on Aug. 20, 2009.

(30) Foreign Application Priority Data

Aug. 20, 2009 (GB) .................................. 0914543.4

(51) Int. Cl.
*A61K 51/00* (2006.01)
*C07K 7/64* (2006.01)

(52) U.S. Cl.
USPC ....... 424/1.69; 424/1.11; 424/1.65; 424/1.85; 424/1.89

(58) Field of Classification Search
USPC ..................... 424/1.11, 1.65, 1.69, 1.85, 1.89
See application file for complete search history.

(56) References Cited

FOREIGN PATENT DOCUMENTS

| WO | 2006/067376 | 6/2006 |
|---|---|---|
| WO | 2006/116629 | 11/2006 |
| WO | 2007/148089 | 12/2007 |
| WO | WO-2007/148089 | * 12/2007 |
| WO | 2009/027707 | 3/2009 |

OTHER PUBLICATIONS

Nwe, et.al. Cancer Biotherapy and Radiopharmaceuticals, vol. 24, No. 3, Jun. 2009 pp. 289-302.
Ku, et.al. Organic Letters, vol. 3, No. 26, 2001, pp. 4185-4187.
Ali, et.al. Synthesis, 1996, pp. 423-445.
Kabalka, et.al. Journal of Labelled Compounds and Radiopharmaceuticals, vol. 48, No. 5, Apr. 1, 2005, pp. 359-362.
Kabalka, et.al. Journal of Labelled Compounds and Radiopharmaceuticals, vol. 50, No. 5-6, Apr. 1, 2007 pp. 446-447.
Eersels, et.al. Journal of Labelled Compounds and Radiopharmaceuticals, vol. 48, No. 4, Mar. 30, 2005, pp. 241-257.
Bolton R, Journal of Labelled Compounds and Radiopharmaceuticals, vol. 45, No. 6, May 1, 2002 pp. 485-528.
Himo, et.al. Journal of the American Chemical Society, vol. 127, No. 1, 2005 pp. 210-216.
PCT/EP20101062149 ISRWO Dated Jan. 4, 2011.
GB0914543.4 Search Report Dated Dec. 24, 2009.

* cited by examiner

*Primary Examiner* — Michael G Hartley
*Assistant Examiner* — Jagadishwar Samala
(74) *Attorney, Agent, or Firm* — Yonggang Ji

(57) ABSTRACT

The present invention provides a novel method of labelling biological targeting molecules (BTMs) of interest with radioiodine. Also provided are novel radioiodinated BTMs prepared using the method, as well as radiopharmaceutical compositions comprising such radioiodinated BTMs. The invention also provides radioiodinated intermediates useful in the method, as well as in vivo imaging methods using.

11 Claims, 3 Drawing Sheets

Figure 1. RP-HPLC analysis [$^{123}$I]-iodoacetylene prepared using peracetic acid.

A = unreacted oxidized iodide
B = $^{123}$I-iodoacetylene
C = $^{123}$I-diiodoacetylene Figure 3. HPLC analysis at *ca.* 10 minutes post distillation showed [$^{123}$I]-iodoacetylene in 94% RCP.
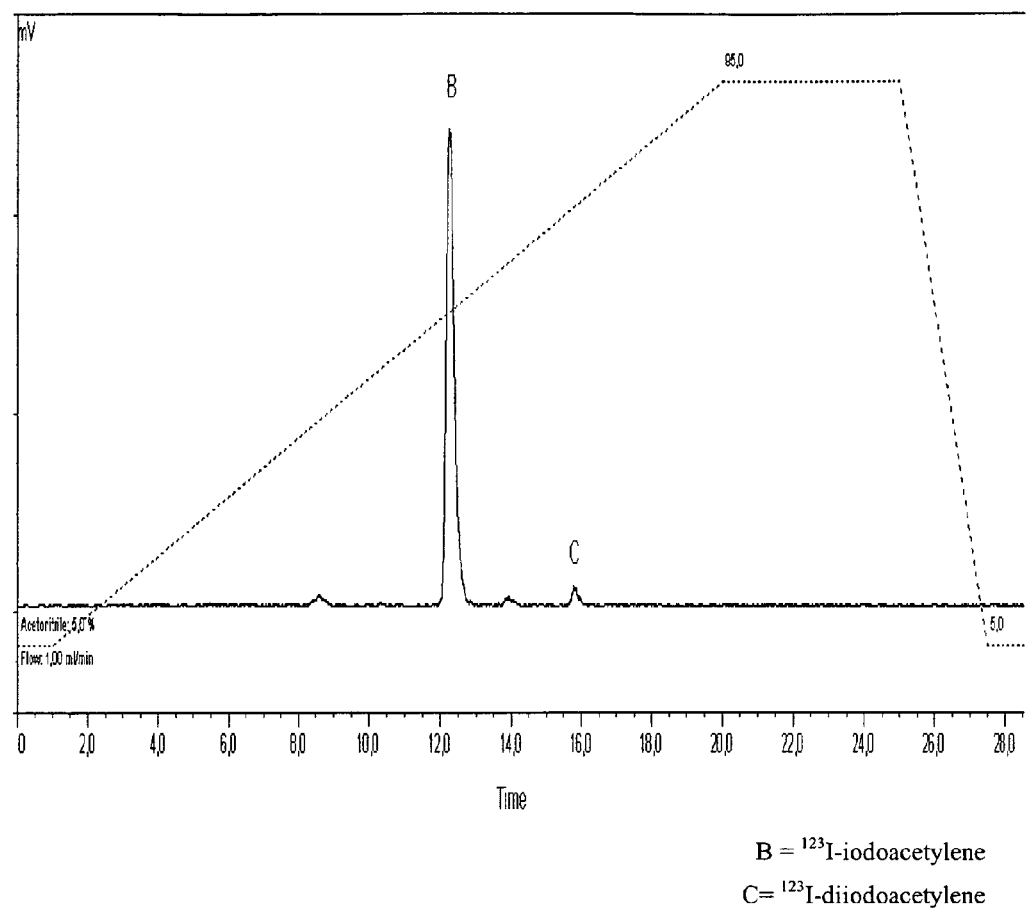
B = $^{123}$I-iodoacetylene
C = $^{123}$I-diiodoacetylene

SEQUENCE LISTING

<160> NUMBER OF SEQ ID NOS: 8

<210> SEQ ID NO 1
<211> LENGTH: 5
<212> TYPE: PRT
<213> ORGANISM: Artificial

```
<220> FEATURE:
<223> OTHER INFORMATION: synthetic peptide

<400> SEQUENCE: 1

Tyr Ile Gly Ser Arg
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Pro Asp Ser Gly Arg
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Ile Lys Val Ala Val
1               5

<210> SEQ ID NO 4
<211> LENGTH: 3
<212> TYPE: PRT
<213> ORGANISM: Artificial
<220> FEATURE:
<223> OTHER INFORMATION: synthetic peptide

<400> SEQUENCE: 4

Leu Arg Glu
1

<210> SEQ ID NO 5
<211> LENGTH: 15
<212> TYPE: PRT
<213> ORGANISM: Artificial
<220> FEATURE:
<223> OTHER INFORMATION: synthetic peptide

<400> SEQUENCE: 5

Lys Cys Gln Ala Gly Thr Phe Ala Leu Arg Gly Asp Pro Gln Gly
1               5                   10                  15

<210> SEQ ID NO 6
<211> LENGTH: 3
<212> TYPE: PRT
<213> ORGANISM: Artificial
<220> FEATURE:
<223> OTHER INFORMATION: synthetic peptide

<400> SEQUENCE: 6

Arg Gly Asp
1

<210> SEQ ID NO 7
<211> LENGTH: 8
<212> TYPE: PRT
<213> ORGANISM: Artificial
<220> FEATURE:
```

```
<223> OTHER INFORMATION: synthetic peptide

<400> SEQUENCE: 7

Asp Arg Val Tyr Ile His Pro Phe
1               5

<210> SEQ ID NO 8
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Sar

<400> SEQUENCE: 8

Xaa Arg Val Tyr Ile His Pro Ile
1               5
```

RADIOIODINATION METHOD

This application is a filing under 35 U.S.C. 371 of international application number PCT/EP2010/062149, filed Aug. 20, 2010, which claims priority to U.S. application No. 61/235,393 filed Aug. 20, 2009 and Great Britain application number 0914543.4 filed Aug. 20, 2009, the entire disclosure of which is hereby incorporated by reference.

FIELD OF THE INVENTION

The present invention provides a novel method of labelling biological targeting molecules (BTMs) of interest with radio-iodine. Also provided are novel radioiodinated BTMs prepared using the method, as well as radiopharmaceutical compositions comprising such radioiodinated BTMs. The invention also provides radioiodinated intermediates useful in the method, as well as in vivo imaging methods using the radioiodinated BTMs.

BACKGROUND TO THE INVENTION

Methods of incorporating radiohalogens into organic molecules are known [Bolton, J. Lab. Comp. Radiopharm., 45, 485-528 (2002)]. For the case of $^{123}$I-labelled radiopharmaceuticals, Eersels et al [J. Lab. Comp. Radiopharm., 48, 241-257 (2005)] have compared the 4 principal synthetic routes:
 (i) oxidative radioiodination;
 (ii) nucleophilic isotopic exchange;
 (iii) nucleophilic non-isotopic exchange;
 (iv) electrophilic labelling.

Route (iv) typically involves the use of an organometallic precursors, such as trialkyltin, trialkylsilyl or organomercury or organothallium derivative. Of these, the radioiododestannylation route was acknowledged as having become the preferred electrophilic labelling method, due to the possibility of regiospecific radioiodination at room temperature. Eersels et al concluded that there was no radioiodination method of choice.

The use of organotin intermediates in radiopharmaceutical synthesis has been reviewed by Ali et at [Synthesis, 423-445 (1996)]. Kabalka et al published extensively on the use of organoborane precursors to permit radioisotope and radiohalogen labelling [see eg. J. Lab. Comp. Radiopharm., 50, 446-447 and 888-894 (2007)].

The applications of "click chemistry" in biomedical research, including radiochemistry, have been reviewed by Nwe et at [Cancer Biother. Radiopharm., 24(3), 289-302 (2009)]. As noted therein, the main interest has been in the PET radioisotope $^{18}$F (and to a lesser extent $^{11}$C), plus "click to chelate" approaches for radiometals suitable for SPECT imaging such as $^{99m}$Tc or $^{111}$In. $^{18}$F click-labelling of targeting peptides, giving products incorporating an $^{18}$F-fluoroalkyl-substituted triazole have been reported by Li et at [Bioconj. Chem., 18(6), 1987-1994 (2007)], and Hausner et at [J. Med. Chem., 51(19), 5901-5904 (2008)].

WO 2006/067376 discloses a method for labelling a vector comprising reaction of a compound of formula (I) with a compound of formula (II):

  (I)

  (II)

Or, a compound of formula (III) with a compound of formula (IV)

  (III)

  (IV)

in the presence of a Cu(I) catalyst, wherein:
 L1, L2, L3, and L4 are each Linker groups;
 R* is a reporter moiety which comprises a radionuclide;
to give a conjugate of formula (V) or (VI) respectively:

  (V)

  (VI)

wherein L1, L2, L3, L4, and R* are as defined above.

R* of WO 2006/067376 is a reporter moiety which comprises a radionuclide for example a positron-emitting radionuclide. Suitable positron-emitting radionuclides for this purpose are said to include $^{11}$C, $^{18}$F, $^{75}$Br, $^{76}$Br, $^{124}$I, $^{82}$Rb, $^{68}$Ga, $^{64}$Cu and $^{62}$Cu, of which $^{11}$C and $^{18}$F are preferred. Other useful radionuclides are stated to include $^{123}$I, $^{125}$I, $^{131}$I, $^{211}$At, $^{99m}$Tc, and $^{111}$In.

WO 2007/148089 discloses a method for radiolabelling a vector comprising reaction of a compound of formula (I) with a compound of formula (II):

  (I)

  (II)

or, a compound of formula (III) with a compound of formula (IV):

  (III)

  (IV)

in the presence of a Cu(I) catalyst, wherein:
 L1, L2, L3, and L4 are each Linker groups;
 R* is a reporter moiety which comprises a radionuclide;
to give a conjugate of formula (V) or (VI) respectively:

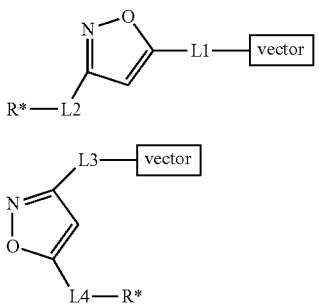

In both WO 2006/067376 and WO 2007/148089, metallic radionuclides are stated to be suitably incorporated into a chelating agent, for example by direct incorporation by methods known to the person skilled in the art. Neither WO 2006/067376 nor WO 2007/148089 discloses any methodology specific for click radioiodination—in particular which combination of compounds of formulae (I)-(IV), together with which combinations of linker groups L1, L2, L3, L4, and which type of R* group would be suitable. In addition, WO 2006/067376 focuses on $^{18}$F, and fluoroacetylene would not be an attractive intermediate for radiolabelling, since it boils at −80° C. and is reported to be explosively unstable in the liquid state [Middleton, J. Am. Chem. Soc., 81, 803-804 (1959)].

WO 2006/116629 (Siemens Medical Solutions USA, Inc.) discloses a method of preparation of a radiolabelled ligand or substrate having affinity for a target biomacromolecule, the method comprising:
(a) reacting a first compound comprising
  (i) a first molecular structure;
  (ii) a leaving group;
  (iii) a first functional group capable of participating in a click chemistry reaction; and optionally,
  (iv) a linker between the first functional group and the molecular structure, with a radioactive reagent under conditions sufficient to displace the leaving group with a radioactive component of the radioactive reagent to form a first radioactive compound;
(b) providing a second compound comprising
  (i) a second molecular structure;
  (ii) a second complementary functional group capable of participating in a click chemistry reaction with the first functional group, wherein the second compound optionally comprises a linker between the second compound and the second functional group;
(c) reacting the first functional group of the first radioactive compound with the complementary functional group of the second compound via a click chemistry reaction to form the radioactive ligand or substrate; and
(d) isolating the radioactive ligand or substrate.

WO 2006/116629 teaches that the method therein is suitable for use with the radioisotopes: $^{124}$I, $^{18}$F, $^{11}$C, $^{13}$N and $^{15}$O with preferred radioisotopes being: $^{18}$F, $^{11}$C, $^{123}$I, $^{124}$I, $^{127}$I, $^{131}$I, $^{76}$Br, $^{64}$Cu, $^{99m}$Tc, $^{90}$Y, $^{67}$Ga, $^{51}$Cr, $^{192}$Ir, $^{99}$Mo, $^{153}$Sm and $^{201}$Tl. WO 2006/116629 teaches that other radioisotopes that may be employed include: $^{72}$As, $^{74}$As, $^{75}$Br, $^{55}$Co, $^{61}$Cu, $^{67}$Cu, $^{68}$Ga, $^{68}$Ge, $^{125}$I, $^{132}$I, $^{111}$In, $^{52}$Mn, $^{203}$Pb and $^{97}$Ru. WO 2006/116629 does not, however, provide any specific teaching on how to apply the method to the radioiodination of biological molecules.

There is therefore still a need for alternative radioiodination methods.

The Present Invention.

The present invention provides methodology for the radioiodination of biological targeting molecules (BTMs), using click radioiodination. The method has the advantage that it can be carried out under mild conditions, and is hence compatible with a range of biological molecules—potentially including such molecules where conventional direct radioiodination methods may be non-viable due to instability of the BTM under the radioiodination reaction conditions. Examples of such sensitivity includes incompatibility or instability with the oxidising conditions necessary for conventional radioiodination. The present method provides radioiodination methodology which can be carried out under non-oxidising conditions, and is hence particularly advantageous for labelling BTMs which are susceptible to oxidation.

The method provides products in which the radioiodine is directly bonded to an triazole or isoxazole heteroaryl ring. The radioiodinated products are thus expected to exhibit good stability with respect to metabolic deiodination in vivo, with consequent unwanted stomach and/or thyroid uptake of radioiodine. The products are therefore suitable for use as radiopharmaceuticals for in vivo imaging, which is an important advantage.

The click radioiodination methodology is readily adaptable to use with an automated synthesizer apparatus. In that regard, the volatility of the iodoacetylene (H—≡—I) used, (predicted to be 32° C. at ca. 1 atmosphere pressure, but reported to be 60-80° C.) can be used advantageously to permit facile distillation of the reactive radioiodine species prior to radiolabelling, so that the radiochemical purity (RCP) of the product is maximised. That minimises the need for further product purification processes, such as via chromatography. It is also in contrast with conventional radioiodination methodology, where volatile radioiodine-containing species (eg. molecular iodine $I_2$) would be regarded as undesirable due to the increased risks of loss of radioactivity and/or radiation dose.

BRIEF DESCRIPTION OF THE DRAWINGS

FIG. 3 shows result of an HPLC analysis at ca. 10 minutes post distillation which showed [$^{123}$I]-iodoacetylene in 94% RCP.

DETAILED DESCRIPTION OF THE INVENTION

Figure 1:
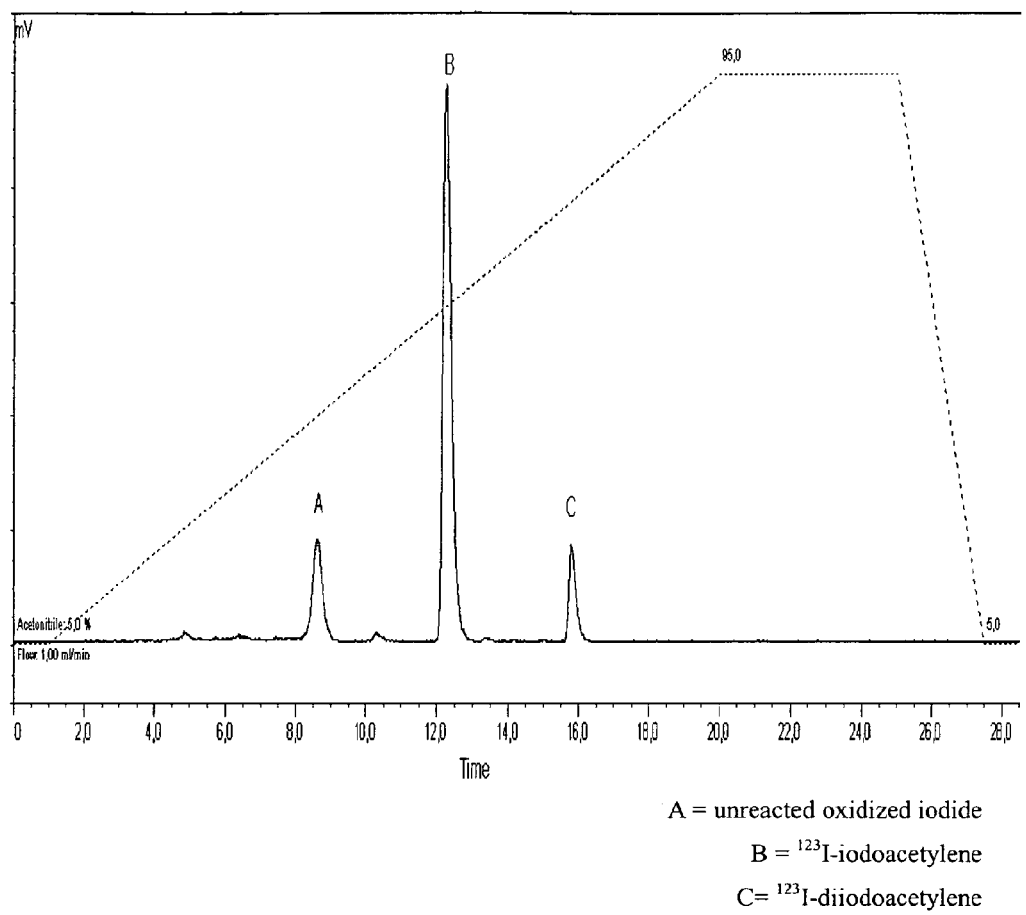
FIG. 1 shows result of the RP-HPLC analysis of [$^{123}$I]-iodoacetylene prepared using peracetic acid.

In a first aspect, the present invention provides a method of radioiodination of a biological targeting moiety, said method comprising:
(i) provision of a compound of Formula (Ia) or (Ib):

(ii) reaction of said compound of Formula (Ia) or (Ib) with a compound of Formula (II):

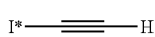
(II)

in the presence of a click cycloaddition catalyst, to give a conjugate of Formula (IIIa) or (IIIb) respectively via click cyclo addition:

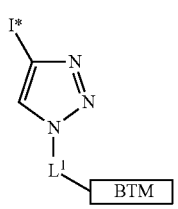
(IIIa)

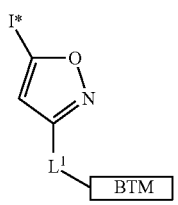
(IIIb)

wherein:
I* is a radioisotope of iodine;
L¹ is a linker group which may be present or absent;
BTM is the biological targeting moiety.

The term "radioiodination" has its conventional meaning, i.e. a radiolabelling process wherein the radioisotope used for the radiolabelling is a radioisotope of iodine.

When the linker group is absent, that means that the azide group of Formula (Ia) or the nitrile oxide functional group of Formula (Ib) is bonded directly to the BTM.

By the term "biological targeting moiety" (BTM) is meant a compound which, after administration, is taken up selectively or localises at a particular site of the mammalian body in vivo. Such sites may for example be implicated in a particular disease state or be indicative of how an organ or metabolic process is functioning.

The term radioisotope of iodine has its conventional meaning, i.e. an isotope of the element iodine that is radioactive. Suitable such radioisotopes include: $^{123}$I, $^{124}$I, $^{125}$I, and $^{131}$I. When the BTM is labelled with $^{131}$I, the product may be useful as a radiopharmaceutical for therapeutic applications in vivo, such as radioimmunotherapy when the BTM is an antibody or antibody fragment.

By the term "click cycloaddition catalyst" is meant a catalyst known to catalyse the click (alkyne plus azide) or click (alkyne plus isonitrile oxide) cycloaddition reaction of the first aspect. Suitable such catalysts are known in the art for use in click cycloaddition reactions. Preferred such catalysts include Cu(I), and are described below. Further details of suitable catalysts are described by Wu and Fokin [Aldrichim. Acta, 40(1), 7-17 (2007)] and Meldal and Tornoe [Chem. Rev., 108, 2952-3015 (2008)].

Preferred Aspects.

A preferred precursor for use in the method of the first aspect is the azide of Formula (Ia), and hence a preferred product is the triazole of Formula (IIIa).

Preferred radioisotopes of iodine for use in the present invention are those suitable for medical imaging in vivo using PET or SPECT, preferably $^{123}$I, $^{124}$I or $^{131}$I, more preferably $^{123}$I or $^{124}$I, most preferably $^{123}$I.

The BTM may be of synthetic or natural origin, but is preferably synthetic. The term "synthetic" has its conventional meaning, i.e. man-made as opposed to being isolated from natural sources eg. from the mammalian body. Such compounds have the advantage that their manufacture and impurity profile can be fully controlled.

Monoclonal antibodies and fragments thereof of natural origin are therefore outside the scope of the term 'synthetic' as used herein.

The molecular weight of the BTM is preferably up to 30,000 Daltons. More preferably, the molecular weight is in the range 200 to 20,000 Daltons, most preferably 300 to 18,000 Daltons, with 400 to 16,000 Daltons being especially preferred. When the BTM is a non-peptide, the molecular weight of the BTM is preferably up to 3,000 Daltons, more preferably 200 to 2,500 Daltons, most preferably 300 to 2,000 Daltons, with 400 to 1,500 Daltons being especially preferred.

The biological targeting moiety preferably comprises: a 3-100 mer peptide, peptide analogue, peptoid or peptide mimetic which may be a linear or cyclic peptide or combination thereof; a single amino acid; an enzyme substrate, enzyme antagonist enzyme agonist (including partial agonist) or enzyme inhibitor; receptor-binding compound (including a receptor substrate, antagonist, agonist or substrate); oligonucleotides, or oligo-DNA or oligo-RNA fragments.

By the term "peptide" is meant a compound comprising two or more amino acids, as defined below, linked by a peptide bond (ie. an amide bond linking the amine of one amino acid to the carboxyl of another). The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. The term "peptide analogue" refers to peptides comprising one or more amino acid analogues, as described below. See also "Synthesis of Peptides and Peptidomimetics", M. Goodman et al, Houben-Weyl E22c, Thieme.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retroinverso peptides, thioamides, cycloalkanes or 1,5-disubstituted tetrazoles [see M. Goodman, Biopolymers, 24, 137, (1985)]. Radio labelled amino acids such as tyrosine, histidine or proline are known to be useful in vivo imaging agents.

When the BTM is an enzyme substrate, enzyme antagonist, enzyme agonist, enzyme inhibitor or receptor-binding compound it is preferably a non-peptide, and more preferably is synthetic. By the term "non-peptide" is meant a compound which does not comprise any peptide bonds, ie. an amide bond between two amino acid residues. Suitable enzyme substrates, antagonists, agonists or inhibitors include glucose and glucose analogues; fatty acids, or elastase, Angiotensin II or metalloproteinase inhibitors. Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

The BTM is most preferably a 3-100 mer peptide or peptide analogue. When the BTM is a peptide, it is preferably a 4-30 mer peptide, and most preferably a 5 to 28-mer peptide.

When the BTM is an enzyme substrate, enzyme antagonist, enzyme agonist or enzyme inhibitor, preferred such biological targeting molecules of the present invention are synthetic, drug-like small molecules i.e. pharmaceutical molecules. Preferred dopamine transporter ligands such as tropanes; fatty acids; dopamine D-2 receptor ligands; benzamides; amphetamines; benzylguanidines, iomazenil, benzofuran (IBF) or hippuric acid. Preferred tropane derivatives are $^{123}$I-CIT (Dopascan™), $^{123}$I-CIT-FP (DaTSCAN™) and the E isomer of [123]I-2β-carbomethoxy-3 β-(4-fluorophenyl)-N-(1-iodoprop-1-en-3-yl)nortropane (Altropane™) Dopascan™ and DaTSCAN™ are especially preferred. These and other tropane agents are described by Morgan and Nowotnik [Drug News Perspect., 12(3), 137-145 (1999). Preferred fatty acids are $^{123}$I-BMIPP and $^{123}$I-IPPA. Preferred amphetamine derivatives are $^{123}$I-IMP. A preferred benzylguanidine is meta-iodobenzylguanidine (MIBG), ie. $^{123}$I-MIBG.

When the BTM is a peptide, preferred such peptides include:

somatostatin, octreotide and analogues,
peptides which bind to the ST receptor, where ST refers to the heat-stable toxin produced by E. coli and other micro-organisms;
bombesin;
vasoactive intestinal peptide;
neurotensin;
laminin fragments eg. YIGSR, PDSGR, IKVAV, LRE and KCQAGTFALRGDPQG,
N-formyl chemotactic peptides for targeting sites of leucocyte accumulation,
Platelet factor 4 (PF4) and fragments thereof,
RGD (Arg-Gly-Asp)-containing peptides, which may eg. target angiogenesis [R. Pasqualini et al., Nat Biotechnol. 1997 June; 15(6):542-6]; [E. Ruoslahti, Kidney Int. 1997 May; 51(5):1413-7].
peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
peptides which are substrates or inhibitors of angiotensin, such as: angiotensin II Asp-Arg-Val-Tyr-Ile-His-Pro-Phe (E. C. Jorgensen et al, *J. Med. Chem.*, 1979, Vol 22, 9, 1038-1044) [Sar, Ile] Angiotensin II: Sar-Arg-Val-Tyr-Ile-His-Pro-Ile (R. K. Turker et al., *Science*, 1972, 177, 1203).
Angiotensin I: Asp-Arg-Val-Tyr-Ile-His-Pro-Phe-His-Leu.

Preferred BTM peptides are RGD peptides. A more preferred such RGD peptide comprises the fragment:

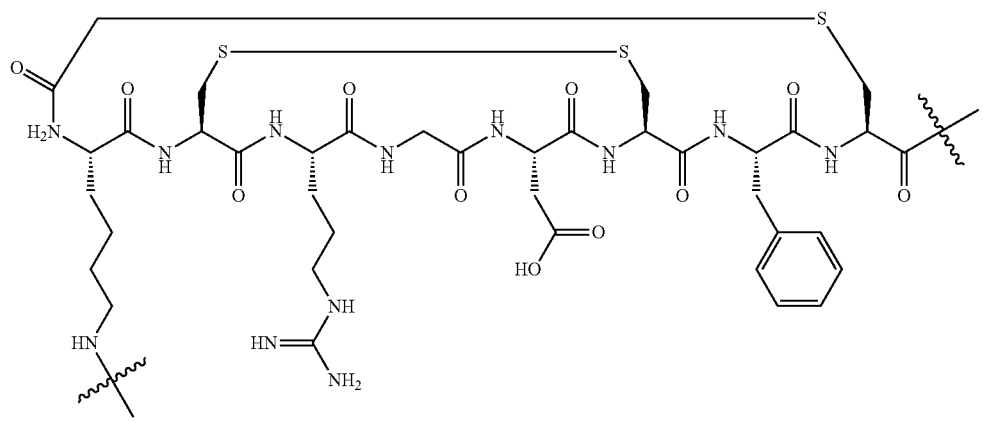 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

A most preferred such RGD peptide is when the BTM is a peptide of formula (A):

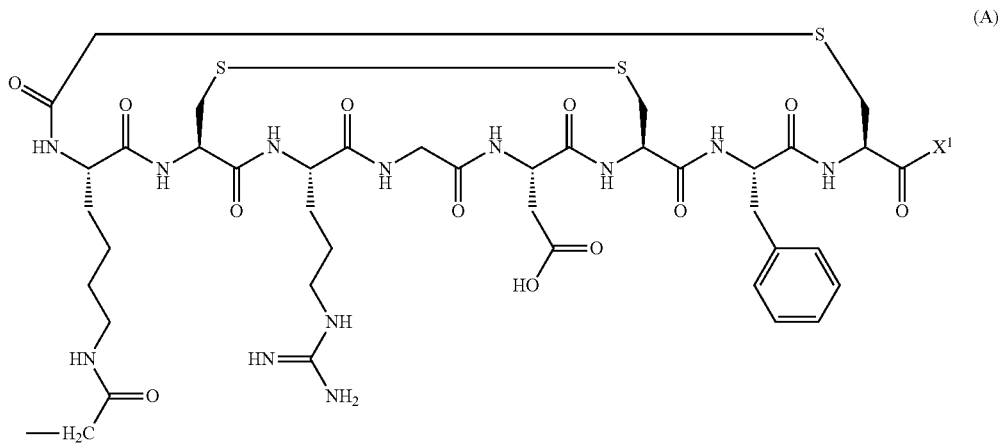

wherein $X^1$ is either —$NH_2$ or

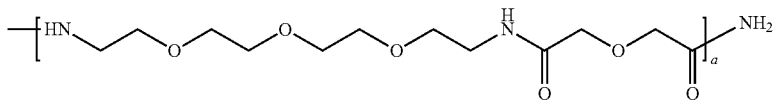

wherein a is an integer of from 1 to 10.

In Formula A, a is preferably 1.

When the BTM is a peptide, one or both termini of the peptide, preferably both, have conjugated thereto a metabolism inhibiting group ($M^{IG}$). Having both peptide termini protected in this way is important for in vivo imaging applications, since otherwise rapid metabolism would be expected with consequent loss of selective binding affinity for the BTM peptide. By the term "metabolism inhibiting group" ($M^{IG}$) is meant a biocompatible group which inhibits or suppresses enzyme, especially peptidase such as carboxypeptidase, metabolism of the BTM peptide at either the amino terminus or carboxy terminus. Such groups are particularly important for in vivo applications, and are well known to those skilled in the art and are suitably chosen from, for the peptide amine terminus:

N-acylated groups —NH(C=O)$R^G$ where the acyl group —(C=O)$R^G$ has $R^G$ chosen from: $C_{1-6}$ alkyl, $C_{3-10}$ aryl groups or comprises a polyethyleneglycol (PEG) building block. Suitable PEG groups are described for the linker group ($L^1$), below. Preferred such PEG groups are the biomodifiers of Formulae Bio1 or Bio2 (below). Preferred such amino terminus $M^{IG}$ groups are acetyl, benzyloxycarbonyl or trifluoroacetyl, most preferably acetyl.

Suitable metabolism inhibiting groups for the peptide carboxyl terminus include: carboxamide, tent-butyl ester, benzyl ester, cyclohexyl ester, amino alcohol or a polyethyleneglycol (PEG) building block. A suitable $M^{IG}$ group for the carboxy terminal amino acid residue of the BTM peptide is where the terminal amine of the amino acid residue is N-alkylated with a $C_{1-4}$ alkyl group, preferably a methyl group. Preferred such $M^{IG}$ groups are carboxamide or PEG, most preferred such groups are carboxamide.

In the method of the first aspect, a linker group ($L^1$) is preferably present. Preferred linker groups ($L^1$) are synthetic, and comprise a group of formula -(A)$_m$- wherein each A is independently —$CR_2$—, —CR=CR—, —C≡C—, —$CR_2CO_2$—, —$CO_2CR_2$—, —NRCO—, —CONR—, —NR(C=O)NR—, —NR(C=S)NR—, —$SO_2NR$—, —$NRSO_2$—, —$CR_2OCR_2$—, —$CR_2SCR_2$—, —$CR_2NRCR_2$—, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block; wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl; and m is an integer of value 1 to 20.

When $L^1$ comprises a peptide chain of 1 to 10 amino acid residues, the amino acid residues are preferably chosen from glycine, lysine, arginine, aspartic acid, glutamic acid or serine. When $L^1$ comprises a PEG moiety, it preferably comprises units derived from oligomerisation of the monodisperse PEG-like structures of Formulae Bio1 or Bio2:

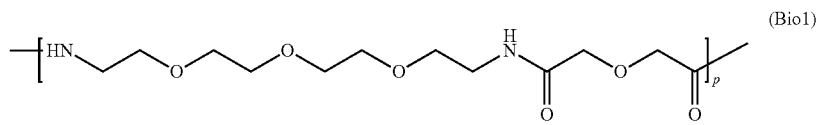

17-amino-5-oxo-6-aza-3,9,12,15-tetraoxaheptadecanoic acid of Formula Bio1 wherein p is an integer from 1 to 10. Alternatively, a PEG-like structure based on a propionic acid derivative of Formula Bio2 can be used:

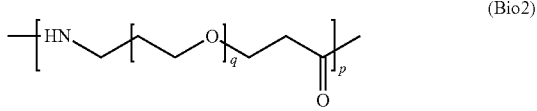

where p is as defined for Formula Bio1 and q is an integer from 3 to 15. In Formula Bio2, p is preferably 1 or 2, and q is preferably 5 to 12.

When the linker group does not comprise PEG or a peptide chain, preferred $L^1$ groups have a backbone chain of linked atoms which make up the -$(A)_m$- moiety of 2 to 10 atoms, most preferably 2 to 5 atoms, with 2 or 3 atoms being especially preferred.

BTM peptides which are not commercially available can be synthesised by solid phase peptide synthesis as described in P. Lloyd-Williams, F. Albericio and E. Girald; *Chemical Approaches to the Synthesis of Peptides and Proteins*, CRC Press, 1997.

In the method of the first aspect, the compound of Formula (II) may preferably be generated in situ by deprotection of a compound of Formula (IIa):

wherein $M^1$ is an alkyne-protecting group, and I* is as defined for Formula (II). Preferred aspects of I* in Formula (IIa), are as described for Formula (II).

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Suitable alkyne protecting groups are described in 'Protective Groups in Organic Synthesis', Theodora W. Greene and Peter G. M. Wuts, Chapter 8, pages 927-933, 4$^{th}$ edition (John Wiley & Sons, 2007), and include: an trialkylsilyl group where each alkyl group is independently $C_{1-4}$ alkyl; an aryldialkylsilyl group where the aryl group is preferably benzyl or biphenyl and the alkyl groups are each independently $C_{1-4}$ alkyl; hydroxymethyl or 2-(2-hydroxypropyl). A preferred such alkyne protecting group is trimethylsilyl. The protected iodoalkynes of Formula IIa have the advantages that the volatility of the radioactive iodoalkyne can be controlled, and that the desired alkyne of Formula (II) can be generated in a controlled manner in situ so that the efficiency of the reaction with the azide derivative of Formula (Ia) or (Ib) is maximised.

The method of the first aspect is preferably carried out in an aseptic manner, such that the product of Formula (IIIa) or (IIIb) is obtained as a radiopharmaceutical composition. Further description of radiopharmaceutical composition is given in the third aspect (below). Thus, the method is carried out under aseptic manufacture conditions to give the desired sterile, non-pyrogenic radiopharmaceutical product. It is preferred therefore that the key components, especially any parts of the apparatus which come into contact with the product of Formula (IIIa) or (IIIb) (eg. vials and transfer tubing) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise the non-radioactive components in advance, so that the minimum number of manipulations need to be carried out on the radioiodinated radiopharmaceutical product. As a precaution, however, it is preferred to include at least a final sterile filtration step.

The compounds of Formula (Ia), (Ib) and (II), plus Cu(I) catalyst and other such reagents and solvents are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. The reaction vessel is suitably chosen from such containers, and preferred embodiments thereof. The reaction vessel is preferably made of a biocompatible plastic (eg. PEEK).

The method of the first aspect is preferably carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical product is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a 'cassette' as described in the eighth aspect (below).

The radioiodination method of the first aspect may be effected in a suitable solvent, for example acetonitrile, a $C_{1-4}$ alkylalcohol, dimethylformamide, tetrahydrofuran, or dimethylsulfoxide, or aqueous mixtures of any thereof, or in water. Aqueous buffers can be used in the pH range of 4-8, more preferably 5-7. The reaction temperature is preferably 5 to 100° C., more preferably at 75 to 85° C., most preferably at ambient temperature (typically 15-37° C.). The click cycloaddition may optionally be carried out in the presence of an organic base, as is described by Meldal and Tornoe [Chem. Rev. 108, (2008) 2952, Table 1 (2008)].

A preferred click cycloaddition catalyst comprises Cu(I). The Cu(I) catalyst is present in an amount sufficient for the reaction to progress, typically either in a catalytic amount or in excess, such as 0.02 to 1.5 molar equivalents relative to the compound of Formula (Ia) or (Ib). Suitable Cu(I) catalysts include Cu(I) salts such as CuI or [Cu(NCCH$_3$)$_4$][PF$_6$], but advantageously Cu(II) salts such as copper (II) sulphate may be used in the presence of a reducing agent to generate Cu(I) in situ. Suitable reducing agents include: ascorbic acid or a salt thereof for example sodium ascorbate, hydroquinone, metallic copper, glutathione, cysteine, Fe$^{2+}$, or Co$^{2+}$. Cu(I) is also intrinsically present on the surface of elemental copper particles, thus elemental copper, for example in the form of powder or granules may also be used as catalyst. Elemental copper, with a controlled particle size is a preferred source of the Cu(I) catalyst. A more preferred such catalyst is elemental copper as copper powder, having a particle size in the range 0.001 to 1 mm, preferably 0.1 mm to 0.7 mm, more preferably around 0.4 mm. Alternatively, coiled copper wire can be used with a diameter in the range of 0.01 to 1.0 mm, preferably 0.05 to 0.5 mm, and more preferably with a diameter of 0.1 mm. The Cu(I) catalyst may optionally be used in the presence of bathophenanthroline, which is used to stabilise Cu(I) in click chemistry.

The non-radioactive precursor compounds of Formula (Ia) and (Ib), wherein the BTM is a peptide or protein may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the alkyne or azide group in a compound of Formula (Ia) or (Ib) may be achieved by reaction of the N or C-terminus of the peptide or with some other functional group contained within the peptide sequence, modification of which does not affect the binding characteristics of the vector. The azide group is preferably introduced by formation of a stable amide bond, for example formed by reaction of a peptide amine function with an activated acid or alternatively reaction of a peptide acid function with an amine function and introduced either during or following the peptide synthesis. Methods for incorporation of an azide group into vectors such as cells, viruses, bacteria may be found in H. C. Kolb and K. B. Sharpless, Drug Discovery Today, Vol 8 (24), December 2003 and the references therein. Suitable bifunctional intermediates useful for incorporation of the azide group in a compound of Formula (Ia) or (Ib) include:

N$_3$-L$^1$-NH$_2$

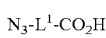
N$_3$-L$^1$-CO$_2$H

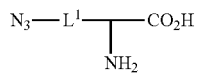

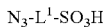
N$_3$-L$^1$-SO$_3$H

N$_3$-L$^1$-OH

N$_3$-L$^1$-SH where L$^1$ and preferred embodiments thereof are as defined above. In the above formulae, L$^1$ is suitably present. In the azide-functionalised amino acid, however, the azide functional group may optionally be attached directly to the side chain of the amino acid without any linker group.

Further approaches to functionalising BTMs with azide groups are described by Nwe et at [Cancer Biother. Radiopharm., 24(3), 289-302 (2009)]. Li et at provide the synthesis of a compound of the type N$_3$-L$^1$-CO$_2$H, where L$^1$ is —(CH$_2$)$_4$— and its use to conjugate to amine-containing BTMs [Bioconj. Chem., 18(6), 1987-1994 (2007)]. Hausner et at describe related methodology for N$_3$-L$^1$-CO$_2$H, where L$^1$ is —(CH$_2$)$_2$— [J. Med. Chem., 51(19), 5901-5904 (2008)]. De Graaf et at [Bioconj. Chem., 20(7), 1281-1295 (2009)] describe non-natural amino acids having azide side chains and their site-specific incorporation in peptides or proteins for subsequent click conjugation.

The nitrile oxides of Formula (Ib) can be obtained by the methods described by Ku et at [Org. Lett., 3(26), 4185-4187 (2001)], and references therein. Thus, they are typically generated in situ by treatment of an alpha-halo aldoxime with an organic base such as triethylamine. See also K. B. G. Torsell "Nitrile Oxides, Nitrones and Nitronates in Organic Synthesis" [VCH, New York (1988)].

The radioiodinated alkynes of Formula (II) and (IIa) can be obtained as described in the fourth aspect (below).

The present invention provides a more chemoselective approach to radioiodination. The ligation reaction occurs at a predetermined site in the BTM, giving only one possible product. This methodology is therefore chemoselective. Additionally, both alkyne and azide functionalities are stable under most reaction conditions and are unreactive with most common peptide functionalities—thus minimising the protection and deprotection steps required during the radiolabelling synthesis. Furthermore, the triazole and isoxazole rings formed during the labelling reaction do not hydrolyse and are highly stable to oxidation and reduction, meaning that the labelled BTM has high in vivo stability. The triazole ring is also comparable to an amide in size and polarity such that the labelled peptides or proteins are good mimics for their natural counterparts—the triazole ring in particular is a known amide mimetic group or bioisostere. The triazole and isoxazole rings of the products of Formula (IIIa) and (IIIb) of the present invention are not, however, expected to be recognized by thyroid deiodination enzymes known to metabolise iodo-tyrosine more rapidly than iodobenzene, and are thus expected to be sufficiently stable in vivo for radiopharmaceutical imaging and radiotherapy.

In a second aspect, the present invention provides a compound of Formula (IIIa) or (IIIb):

(IIIa)

(IIIb)

where I*, $L^1$ and BTM and preferred embodiments thereof are as defined in the first aspect. In particular, $L^1$ may be present or absent.

Preferably, the compound of the second aspect is of Formula (IIIa).

The present invention also provides a compound of Formula (IIIa) or (IIIb) as defined in the second aspect for medical use—preferably the compound of Formula (IIIa).

In a third aspect, the present invention provides a radiopharmaceutical composition comprising an effective amount of a compound of Formula (IIIa) or (IIIb) according to the second aspect, together with a biocompatible carrier medium. Preferred embodiments of I*, $L^1$ and BTM are as defined in the first aspect (above). The compound of the third aspect is also preferably a triazole of Formula (IIIa).

The "biocompatible carrier medium" comprises one or more pharmaceutically acceptable adjuvants, excipients or diluents. It is preferably a fluid, especially a liquid, in which the compound of Formula (IIIa) or (IIIb) is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

In a fourth aspect, the present invention provides a method of preparation of the compound of Formula II as defined in the first aspect, which comprises:

(i) reaction of a precursor of either Formula IV or Formula V

(IV)

(V)

wherein $M^2$ is H or an $M^1$ group, and $M^1$ is as defined in the first aspect, and each $R^a$ is independently $C_{1-4}$ alkyl;

with a supply of radioactive iodide ion in the presence of an oxidising agent, to give a compound of Formula IIb:

(IIb)

where I* is as defined in the first aspect;

(ii) when $M^2$ is an $M^1$ group, deprotection to remove the $M^1$ group.

Protecting groups $M^1$ suitable for use in the fourth aspect, and preferred embodiments thereof are as described in the first aspect (above). Deprotection conditions are described in 'Protective Groups in Organic Synthesis', Theodora W. Greene and Peter G. M. Wuts, Chapter 8, pages 927-933, 4th edition (John Wiley & Sons, 2007).

The precursor of Formula IV or V is non-radioactive. Some precursors of Formula (IV) are commercially available. Thus, the trialkyltin compounds $Bu_3Sn$—≡—H and $Bu_3Sn$—≡—$SiMe_3$ are commercially available from Sigma-Aldrich. Other organotin intermediates are described by Ali et at [Synthesis, 423-445 (1996)]. Suitable oxidising agents are described by Bolton [J. Lab. Comp. Radiopharm., 45, 485-528 (2002)]. Preferred oxidising agents are peracetic acid (which is commercially available) at pH ca. 4, and hydrogen peroxide/aqueous HCl at pH ca. 1. When $M^2$ is H, the compound of Formula IIb is iodoacetylene. The synthesis of the non-radioactive ($^{127}$I) analogue has been described by Ku et at [Org. Lett., 3(26), 4185-4187 (2001)]. The synthesis of $^{123}$I-labelled alkynyl iodides via the potassium alkynyltrifluoroborate precursors analogous to Formula (V), using peracetic acid in the radioiodination step, has been described by Kabalka et al [J. Lab. Comp. Radiopharm., 48, 359-362 (2005)]. The synthesis of potassium alkynyltrifluoroborate precursors from the corresponding alkyne is described therein, as well as in Kabalka et at [J. Lab. Comp. Radiopharm., 49, 11-15 (2006)]. The potassium alkynyltrifluoroborate precursors are stated to be crystalline solids, which are stable to both air and water.

In a fifth aspect, the present invention provides a compound of Formula (IIb), useful in the method of the first aspect:

(IIb)

where I* is as defined for the first aspect; and $M^2$ is H or $M^1$, wherein $M^1$ is as defined for Formula IIa (above).

Preferred embodiments of I* and $M^1$ are as defined in the first aspect (above).

When $M^2$ is H, the compound of Formula (IIb) is radioiodinated iodoacetylene. The volatility of the iodoacetylene (H—≡—I) used, 32° C. at 1 atmosphere pressure, can be used advantageously to permit facile distillation of the reactive radioiodine species prior to radiolabelling, with the product trapped e.g. in a vessel cooled in dry ice. That represents a useful purification prior to the radioiodination step. Since the click cycloaddition is high-yielding, it is anticipated that all of Compound (II) would be consumed, hence the radiochemical purity (RCP) of the product, i.e. Compound (IIIa) or (IIIb), is maximised.

In a sixth aspect, the present invention provides the use of a compound according to the second or fifth aspects, for the manufacture of a radiopharmaceutical for use in a method of in vivo imaging or in vivo radiotherapy. Preferably, the use is in a method of in vivo imaging, more preferably imaging via PET or SPECT.

In a seventh aspect, the present invention provides the use of an automated synthesizer apparatus to carry out the method of the first or fourth aspects.

The automated synthesizer apparatus and preferred embodiments thereof are as described in the first aspect (above).

In an eighth aspect, the present invention provides a single use, sterile cassette suitable for use in the automated synthesizer of the preferred embodiment of the first aspects, said cassette comprising the non-radioactive reagents necessary to carry out the method of the first or fourth aspect in sterile, apyrogenic form.

Preferred embodiments of the above methods for use in the eighth aspect are as described in the first and fourth aspects respectively.

By the term "cassette" is meant a piece of apparatus designed to fit removably and interchangeably onto an automated synthesizer apparatus (as defined below), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. SPE). The cassette always comprises a reaction vessel. Such reaction vessels are preferably 1 to 10 cm³, most preferably 2 to 5 cm³ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes of the present invention are designed to be suitable for radiopharmaceutical manufacture and are therefore manufactured from materials which are of pharmaceutical grade and ideally also are resistant to radiolysis.

Preferred automated synthesizers of the present invention are those which comprise a disposable or single use cassette which comprises all the reagents, reaction vessels and apparatus necessary to carry out the preparation of a given batch of radioiodinated radiopharmaceutical. The cassette means that the automated synthesizer has the flexibility to be capable of making a variety of different radioiodine-labelled radiopharmaceuticals with minimal risk of cross-contamination, by simply changing the cassette. The cassette approach also has the advantages of: simplified set-up hence reduced risk of operator error; improved GMP compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In a ninth aspect, the present invention provides method of generating an image of a human or animal body comprising administering a compound according to the second aspect, or the radiopharmaceutical composition according to the fifth aspect and generating an image of at least a part of said body to which said compound or composition has distributed using PET or SPECT.

In a further aspect, the present invention provides a method of monitoring the effect of treatment of a human or animal body with a drug, said method comprising administering to said body a compound according to the second aspect, or the composition according to the fifth aspect, and detecting the uptake of said compound or composition in at least a part of said body to which said compound or composition has distributed using PET or SPECT.

The administration and detection of this final aspect are preferably effected before and after treatment with said drug, so that the effect of the drug treatment on the human or animal patient can be determined. Where the drug treatment involves a course of therapy, the imaging can also be carried out during the treatment.

The invention is illustrated by the following Examples. Example 1 provides the synthesis for a reference sample of non-radioactive ($^{127}$I) iodo-acetylene as an authentic reference standard for chromatography. Example 2 provides the click coupling of iodo-acetylene with benzyl azide, to form a triazole ring. Examples 3 to 5 provide the synthesis of $^{123}$I-iodoacetylene using different oxidants. Examples 6 to 8 provide prophetic examples of the synthesis of radioiodinated triazoles using the method of the invention. Example 9 provides a prophetic example of the synthesis of radioiodinated triazoles using the method of the invention.

Abbreviations.

DIPEA: di-isopropylethylamine

DMF: Dimethylformamide

HPLC: High performance liquid chromatography

MeCN: Acetonitrile

PAA: Peracetic acid

RP-HPLC: reverse-phase HPLC,

RT: room temperature

THF: tetrahydrofuran.

EXAMPLE 1

Synthesis of Iodo Acetylene

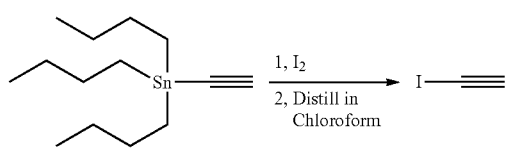

Tributyl(ethynyl)stannane (Sigma-Aldrich; 400 mg, 1.27 mmol) in deuterochloroform (2 ml) at 0° C. was treated with iodine (322 mg, 1.27 mmol). The reaction was then allowed to warm to room temperature over a period of 15 min when the colour of the iodine rapidly faded. The reaction was then distilled, and the volatile iodoacetylene in deuterochloroform collected as a colourless liquid. NMR in chloroform indicated that it was a pure solution of iodoacetylene. Yield cannot easily be estimated on this scale, as iodoacetylene is a volatile material.

$^1$H NMR (300 MHz, CDCl$_3$): $\delta_H$ 2.17 (1H, s, CH). $^{13}$C NMR (75 MHz, CDCl$_3$): $\delta_C$ 83.3, (other carbon not visible).

EXAMPLE 2

Synthesis of 1-benzyl-4-iodo-1H-1,2,3-triazole

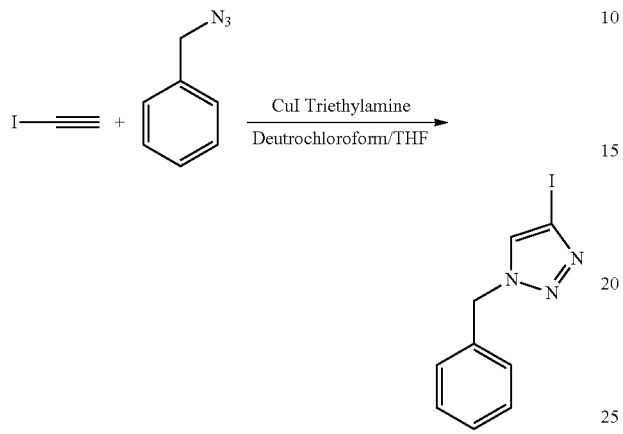

A solution of iodoacetylene (193 mg, 1.27 mmol, assuming 100% yield from previous reaction) in deuterochloroform (2 ml) and THF (2 ml) at 20° C. was treated with azidomethyl benzene (benzyl azide; 169 mg, 1.27 mmol) [commercially available from Alfa Aeser; Fr. Moulin, Helvet. Chim. Acta, 35, 167-80 (1952)], copper iodide (90 mg, 0.47 mmol), and triethylamine (256 mg, 2.54 mmol). The reaction was then stirred at room temperature over a period of 48 h. The reaction was then filtered through celite to remove copper (I) oxide and then chromatographed on silica in a gradient of 15-50% ethyl acetate in petrol. Two fractions were collected. Fraction 1 was evaporated to give a colourless oil (102 mg, 0.77 mmol).

$^1$H NMR and $^{13}$C NMR indicated that this was mainly unreacted azidomethyl benzene.

Fraction 2 was evaporated to give 1-benzyl-4-iodo-1H-1, 2,3-triazole as a colourless liquid that crystallized on standing (104 mg, 0.364 mmol, 28%).

$^1$H NMR (300 MHz, CDCl$_3$): $\delta_H$ 5.60 (2H, s, CH$_2$), 7.24 (2H, m, 2×ArH) 7.32 (3H, m, 3×ArH), 7.741H, s, CHArH). $^{13}$C NMR (75 MHz, CDCl$_3$): $\delta_C$ 53.8, 127.7, 128.4, 128.8. 134.2 141.5. One carbon not visible.

EXAMPLE 3

Preparation and Distillation of [$^{123}$I]-Iodoacetylene Using Peracetic Acid Oxidant

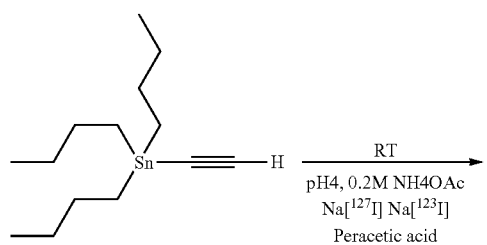

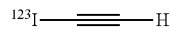

To a Wheaton vial on ice was added, ammonium acetate buffer (100 µl, 0.2M, pH 4), sodium [$^{127}$I] iodide (10 µl, 10 mM solution in 0.01M sodium hydroxide, 1×10$^{-7}$ moles), sodium [$^{123}$I] iodide (10 µl, 20-85 MBq), peracetic acid, (10 µl, 10 mM solution, 1×10$^{-7}$ moles) and a solution of ethynyl-tributylstannane in THF (Sigma-Aldrich; 100 µl, 0.38 mg/ml, 1.2×10$^{-7}$ moles). Finally, 400-600 µl THF was added, the Wheaton vial sealed and the reaction mixture allowed to warm to room temperature prior to reverse phase HPLC analysis.

HPLC analysis at ca. 10 minutes post addition of ethynyl-tributylstannane yielded [$^{123}$I]-iodoacetylene with a radiochemical purity (RCP) of 75%. See FIG. 1. The impurity with the longer retention time is believed to be $^{123}$I-diidoacetylene.

Figure 2:
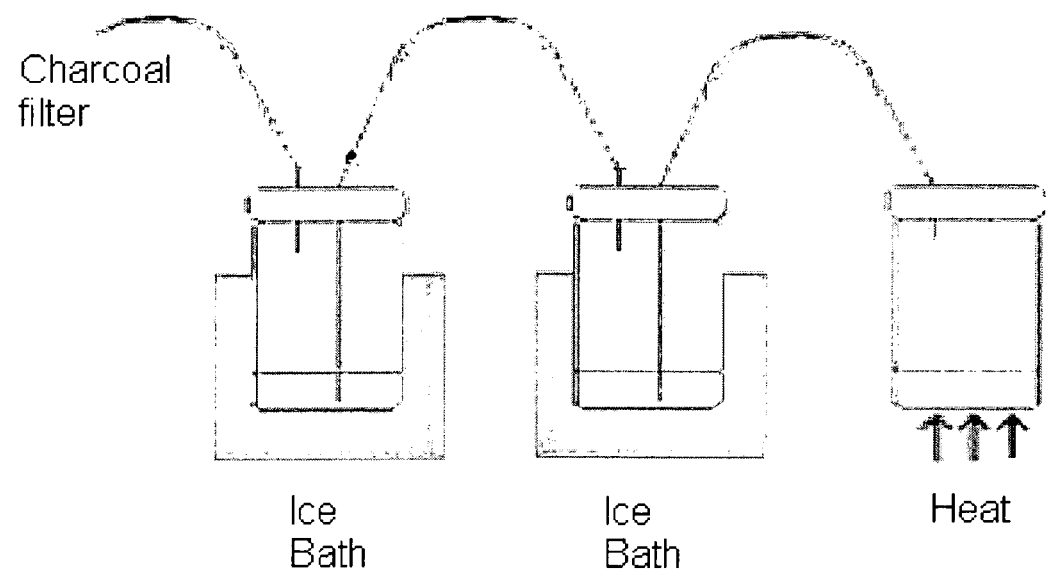
FIG. 2 shows a diagram of a distillation apparatus according to certain embodiments of the invention.

The reaction mixture was heated at 80-100° C. for 15-20 minutes during which time, the [$^{123}$I]-iodoacetylene and THF were distilled through a short tube into a collection vial on ice. After this time, a low flow of nitrogen was passed through the septa of the heated vial to remove any residual liquids from the tube. See FIG. 2.

HPLC analysis at ca. 10 minutes post distillation showed [$^{123}$I]-iodoacetylene in 94% RCP. See FIG. 3.

EXAMPLE 4

Preparation of [$^{123}$I]-Iodoacetylene Using Iodo-Gen Tubes

To an iodo-gen tube (Thermo Scientific Pierce Protein Research Products) pre-wet with sodium phosphate buffer (1 ml pH 7.4, 25 mM), was added sodium phosphate buffer (100 µl pH 7.4, 25 mM), sodium [$^{127}$I] iodide (10 µl, 10 mM solution in 0.01M sodium hydroxide, 1×10$^{-7}$ moles) and sodium [$^{123}$I] iodide (10 µl, 18 MBq). Following incubation at room temperature for 6 minutes, the said reactants were transferred to a Wheaton vial on ice prior to the addition of a solution of ethynyltributylstannane in THF, (Sigma-Aldrich; 38 µl, 1 mg/ml, 1.2×10$^{-7}$ moles). The vial was sealed and the reaction mixture allowed to warm to room temperature prior to reverse phase HPLC analysis.

HPLC analysis at ca. 10 minutes post addition of ethynyl-tributylstannane, showed [$^{123}$I]-iodoacetylene in 57% yield.

EXAMPLE 5

Preparation and Purification of [$^{123}$I]-Iodoacetylene Using Hydrogen Peroxide Oxidant To a Wheaton vial on ice was added, sodium [$^{127}$I] iodide (10 µl, 10 mM solution in 0.01M sodium hydroxide, 1×10$^{-7}$ moles), sodium [$^{123}$I] iodide (10 µl, 18 MBq), hydrochloric acid (100 µl, 1M), hydrogen peroxide (50 µl, 3% solution in water, 4.4×10$^{-5}$ moles) and a solution of ethynyltributylstannane in THF (Sigma-Aldrich; 38 µl, 1 mg/ml, 1.2×10$^{-7}$ moles). The was vial sealed and the reaction mixture allowed to warm to room temperature prior to reverse phase HPLC analysis.

HPLC analysis at ca. 10 minutes post addition of ethynyl-tributylstannane, yielded [$^{123}$I]-iodoacetylene in 85% yield.

EXAMPLE 6

Preparation of 1-Benzene-4-[$^{123}$I]-iodo-1H-1,2,3-triazole (Prophetic Example)

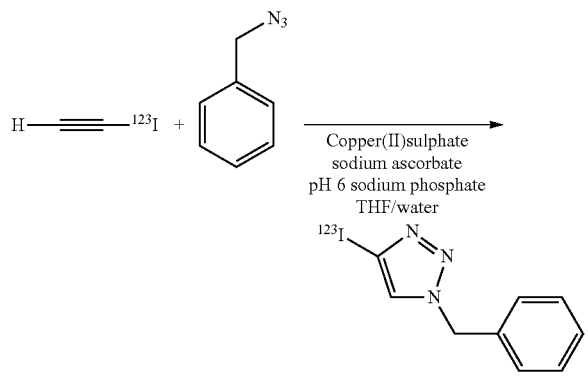

To a cooled Wheaton vial containing [$^{123}$I]-iodoacetylene in THF (Example 3, 4 or 5) is added, water, copper sulphate, sodium L ascorbate and sodium phosphate buffer. Finally, a solution of benzyl azide is added and the ice bath removed. The reaction is incubated at room temperature with heating applied as required. After dilution in water, the 1-Benzene-4-[$^{123}$I]-iodo-1H-1,2,3-triazole is purified by reverse phase HPLC or Sep-Pak cartridge.

EXAMPLE 7

Preparation of 1-Benzene-4-[$^{123}$I]-iodo-1H-1,2,3-triazole (Prophetic Example)

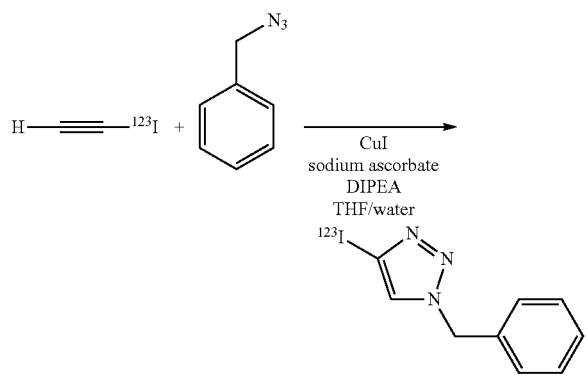

To a Wheaton vial on ice containing [$^{123}$I]-iodoacetylene in THF (Example 3, 4 or 5) is added, copper (I) iodide, sodium L ascorbate, water and di-isopropylethylamine. Finally, a solution of benzyl azide is added and the ice bath removed. The reaction is incubated at room temperature with heating applied as required. After dilution in water, the 1-Benzene-4-[$^{123}$I]-iodo-1H-1,2,3-triazole is purified by reverse phase HPLC or Sep-Pak cartridge.

EXAMPLE 8

Preparation of 1-Benzene-4-[$^{123}$I]-iodo-1H-1,2,3-triazole (Prophetic Example)

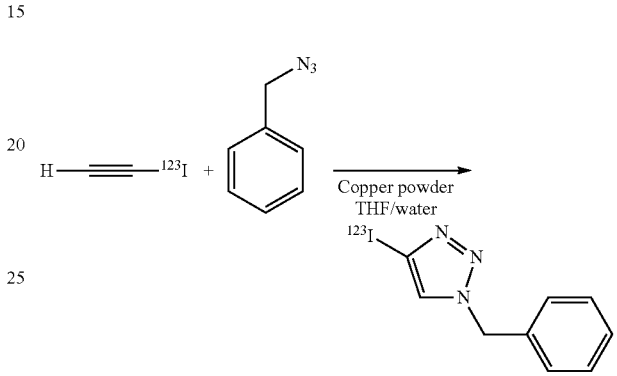

To a Wheaton vial charged with copper powder (~40 mesh) and placed on ice is added, [$^{123}$I]-iodoacetylene (Example 3, 4 or 5) and benzyl azide. Following reagent addition, the ice bath is removed and the reaction incubated at room temperature with heating applied as required.

EXAMPLE 9

Preparation of Radioiodinated Isoxazoles (Prophetic Example)

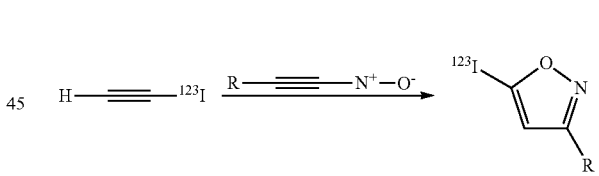

To the cooled 3 ml Wheaton vial containing [$^{123}$I]-iodoacetylene (Example 3, 4 or 5) is added a solution of the nitrile oxide dissolved in THF (0.1-0.5 ml). The reaction mixture is further stirred at 0° C. for 15 minutes before being allowed to warm up to room temperature and stirring for a further 30-60 minutes until all the iodoacetylene has been consumed. After dilution in water, the [$^{123}$I] isoxazole is purified by HPLC.

---

What is claimed is:

1. A method of radioiodination of a biological targeting moiety, said method comprising:

(i) provision of a compound of Formula (Ia) or (Ib):

   (Ia)

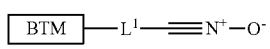   (Ib)

(ii) reaction of said compound of Formula (Ia) or (Ib) with a compound of Formula (II):

   (II)

in the presence of a click cycloaddition catalyst, to give a conjugate of Formula (IIIa) or (IIIb) respectively via click cycloaddition:

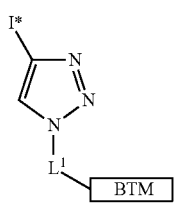   (IIIa)

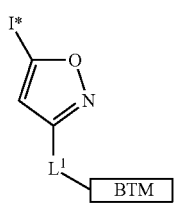   (IIIb)

wherein:
I* is a radioisotope of iodine;

$L^1$ comprises a group of formula $-(A)_m-$ wherein each A is independently $-CR_2-$, $-CR=CR-$, $-C\equiv C-$, $-CR_2CO_2-$, $-CO_2CR_2-$, $-NRCO-$, $-CONR-$, $-NR(C=O)NR-$, $-NR(C=S)NR-$, $-SO_2NR-$, $-NRSO_2-$, $-CR_2OCR_2-$, $-CR_2SCR_2-$, $-CR_2NRCR_2-$, a $C_{4-8}$ cycloheteroalkylene group, a $C_{4-8}$ cycloalkylene group, a $C_{5-12}$ arylene group, or a $C_{3-12}$ heteroarylene group, an amino acid, a sugar or a monodisperse polyethyleneglycol (PEG) building block;

wherein each R is independently chosen from: H, $C_{1-4}$ alkyl, $C_{2-4}$ alkenyl, $C_{2-4}$ alkynyl, $C_{1-4}$ alkoxyalkyl or $C_{1-4}$ hydroxyalkyl;

and m is an integer of value 1 to 20;

BTM is the biological targeting moiety chosen from: a single amino acid, a 3-100 mer peptide, an enzyme substrate, an enzyme antagonist, an enzyme agonist, an enzyme inhibitor or a receptor-binding compound.

2. The method according to claim 1, wherein I* is chosen from $^{123}$I, $^{124}$I or $^{131}$I.

3. The method according to claim 1 wherein BTM is an RGD peptide.

4. The method according to claim 1, wherein BTM is a peptide comprising the fragment:

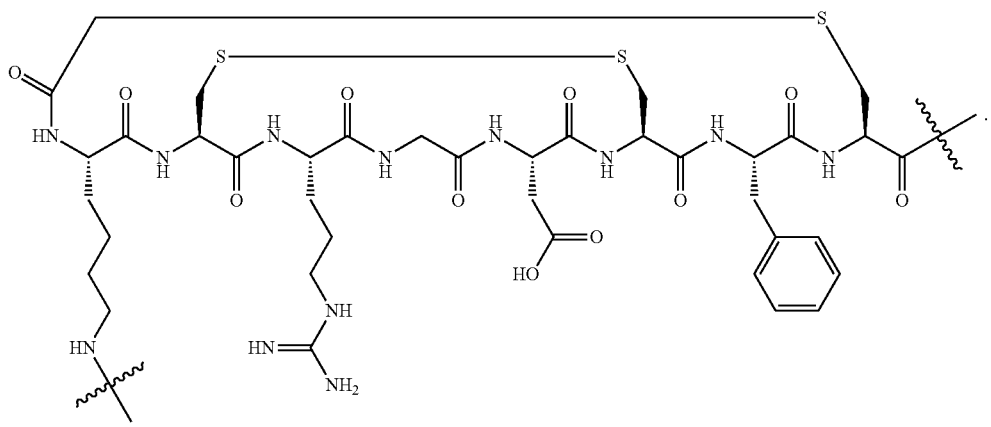 [SMILES: *NCCCC[C@@H]1NC(=O)CSC[C@@H](C(*)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

5. The method according to claim 1 where BTM is a peptide of formula (A):

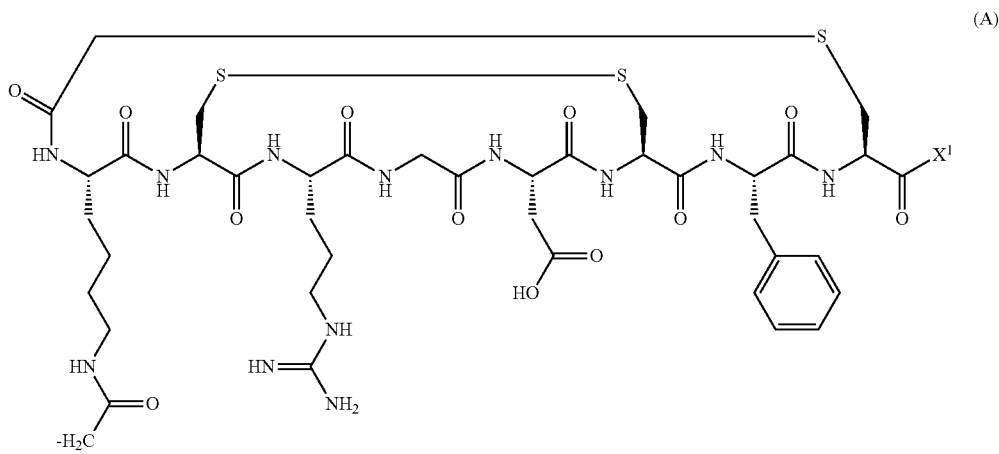

wherein $X^1$ is either —NH$_2$ or

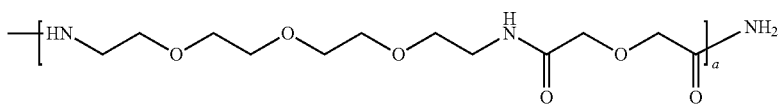

wherein a is an integer of from 1 to 10.

6. The method according to claim 1, wherein the click cycloaddition catalyst is a Cu(I) catalyst and comprises elemental copper.

7. The method according to claim 6, wherein the elemental copper has a particle size in the range from 0.001 to 1 mm.

8. The method of claim 1, where the compound of Formula (II) is generated in situ by deprotection of a compound of Formula (IIa):

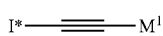

wherein $M^1$ is an alkyne-protecting group.

9. The method of claim 1, which is carried out in an aseptic manner, such that the product of Formula (IIIa) or (IIIb) is obtained as a radiopharmaceutical composition.

10. A compound of Formula (IIIa) or (IIIb):

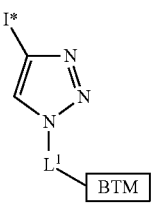

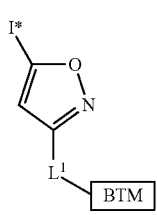
(IIIb)
where I* and L¹ are as defined in claim 1, and BTM is as defined in claim 1.
11. A radiopharmaceutical composition comprising an effective amount of a compound according to claim 10, together with a biocompatible carrier medium.
* * * * *